(12) United States Patent
Souther et al.

(10) Patent No.: US 10,159,510 B2
(45) Date of Patent: Dec. 25, 2018

(54) INTRAVAGINAL FERTILITY DEVICE

(71) Applicant: Truth in Design, Inc., San Francisco, CA (US)

(72) Inventors: Sherman Souther, San Francisco, CA (US); Hamilton Souther, Evergreen, CO (US)

(73) Assignee: Truth in Design, Inc., San Francisco, CA (US)

( * ) Notice: Subject to any disclaimer, the term of this patent is extended or adjusted under 35 U.S.C. 154(b) by 158 days.

(21) Appl. No.: 15/210,252

(22) Filed: Jul. 14, 2016

(65) Prior Publication Data

US 2018/0014854 A1  Jan. 18, 2018

(51) Int. Cl.
*A61B 17/425* (2006.01)
*A61B 17/43* (2006.01)

(52) U.S. Cl.
CPC .................................... *A61B 17/43* (2013.01)

(58) Field of Classification Search
CPC .................................................... A61B 17/425
See application file for complete search history.

(56) References Cited

U.S. PATENT DOCUMENTS

| 2,855,932 | A | 10/1958 | Stubbs |
| 3,910,275 | A | 10/1975 | Babey et al. |
| 4,993,432 | A | 2/1991 | Shields et al. |
| 5,674,178 | A | 10/1997 | Root |
| 5,853,362 | A * | 12/1998 | Jacobs ............... A61H 19/44 600/38 |
| 7,056,279 | B2 | 6/2006 | Verberckmoes et al. |
| 7,165,550 | B1 | 1/2007 | Tracy |
| 8,454,493 | B2 | 6/2013 | La Vean |
| 8,728,140 | B2 | 5/2014 | Feemster et al. |
| 8,764,623 | B2 | 7/2014 | Minow |
| 8,979,734 | B2 | 3/2015 | Minnow |
| 2005/0028824 | A1 | 2/2005 | Jordan et al. |
| 2005/0228218 | A1 * | 10/2005 | Skidmore ............... A61H 19/44 600/38 |
| 2010/0179378 | A1 | 7/2010 | Chen |
| 2010/0210898 | A1 | 8/2010 | Noble et al. |
| 2011/0087065 | A1 | 4/2011 | Liu |
| 2012/0136204 | A1 | 5/2012 | Hidalgo-Mendoza |

(Continued)

FOREIGN PATENT DOCUMENTS

| CN | 204951110 U | 1/2016 |
| ES | 2323830 | 7/2009 |

(Continued)

OTHER PUBLICATIONS

New Clinical Study Demonstrates Stork OTC Home Conception Kit is More Effective at Delivering, Business Wire, Dec. 3, 2015, New York.

*Primary Examiner* — Christine H Matthews
*Assistant Examiner* — Joshua D Lannu
(74) *Attorney, Agent, or Firm* — Marton Ribera Schumann & Chang LLP (57) ABSTRACT

A device and method for improving fertility among couples after intercourse is disclosed. The device and method uses an intravaginal device that collects ejaculate from the vaginal canal after intercourse and presents it to the os of the cervix. The device also serves to contain ejaculate near the cervical os to increase the chances of successful fertilization.

13 Claims, 9 Drawing Sheets

(56) References Cited

U.S. PATENT DOCUMENTS

| | | | |
|---|---|---|---|
| 2012/0143001 A1* | 6/2012 | Case | A61F 5/455 600/38 |
| 2015/0196324 A1 | 7/2015 | Kanner et al. | |
| 2015/0282916 A1 | 10/2015 | Stroud | |

FOREIGN PATENT DOCUMENTS

| | | |
|---|---|---|
| GB | 2462273 | 2/2010 |
| WO | WO2001017443 | 3/2001 |

* cited by examiner

INTRAVAGINAL FERTILITY DEVICE

FIELD OF THE INVENTION

This disclosure generally relates to the field of fertility devices, and in particular, an intravaginal fertility device for collecting and presenting ejaculate closer to the cervix.

BACKGROUND OF THE INVENTION

According to the National Institutes of Health, fifteen percent of couples are unable to get pregnant after twelve months of regular unprotected sexual intercourse. There are many potential reasons for reduced fecundity; one third of the cases involve male infertility, another third female infertility, with the balance involving both. Conventional therapies for fertility problems typically include medication or surgery. Both of these categories of therapies can pose health risks. Fertility medications may have undesirable side-effects and can be expensive. Surgical treatments may be seen as too invasive and risky; other treatments, such as assistive reproductive technology, may also present a level of invasiveness and expense that puts it out of reach of many couples searching for fertility assistance.

Others have proposed various intravaginal devices to provide less invasive and expensive fertility treatments. These devices include artificial insemination, cervical cap, and intravaginal plug devices. Artificial insemination devices require collection and subsequent introduction of semen to the vaginal canal and cervix by mechanical methods, such as the use of a catheter with a plunger or syringe. See, e.g., U.S. Patent Application No. 2011/0087065; 2015/0196324. Existing cervical cap devices for improving fertility also require collection of semen prior to insertion of the cup, which stays in place at the cervix for up to six hours. But collection and handling of semen can be complicated and difficult, and must be carried out in a manner that will not damage the semen. Intravaginal plugs, such as that proposed in U.S. Publication No. 2005/0028824, while less complicated and easier to use than artificial insemination and cervical cap devices, are designed to keep the ejaculate from exiting the vaginal canal; however, these devices are not specifically designed to place the ejaculate in contact with the cervix and uterus, and any such contact is incidental to their use.

What is needed is a method and apparatus for improving the potential for pregnancy without the invasive and complex procedures currently proposed or available.

SUMMARY OF THE INVENTION

The present invention solves the above problems with an intravaginal device comprised of rigid and elastically-deformable portions that is inserted into the vaginal canal after intercourse. In one embodiment, the device has a rigid longitudinal shaft attached to a round, concave end cup; after intercourse, the device is inserted into the vagina and moved gently up the vaginal canal toward the cervix. As it moved, the end cup of the device makes contact with the walls of the vaginal canal to collect and present ejaculate including semen to the os of the cervix. The device is left in the vagina for up to twenty minutes, then removed using the rigid shaft.

In another embodiment of the present invention similar to the above described embodiment, the device is formed using an elastically-deformable material over a rigid shaft or spine. The elastically-deformable material forms a concave cup and the end for collection and presentation of ejaculate to the os of the cervix in a manner similar to that described above in the first embodiment.

In another embodiment of the present invention, an expandable end cup is attached to a longitudinal shaft which is movably positioned in a rigid plastic shell. The shell and cup of the device is inserted into the vagina. The shaft is then moved longitudinally, causing the end cup to exit the shell, and expand to contact the walls of the vaginal canal. As the expanded cup is moved by the shaft toward the cervix, the cup collects ejaculate from the walls of the vaginal canal and presents it to the os of the cervix.

In yet another embodiment, the end cup of the device detaches from the shaft. When assembled into the unit prior to use, the cup is folded so as to create a smaller profile, thereby easier to insert into the entrance of the vagina. After insertion into the vagina, the cup unfolds to its full diameter, which allows the sides of the cup to contact the walls of the vaginal canal, collect ejaculate and present it to the os of the cervix. Then the shaft can be separated from the cup and removed from the vagina. After an amount of time has passed, the cup can be removed from the vagina via a wire connected to the cup.

DETAILED DESCRIPTION

Figure 1:
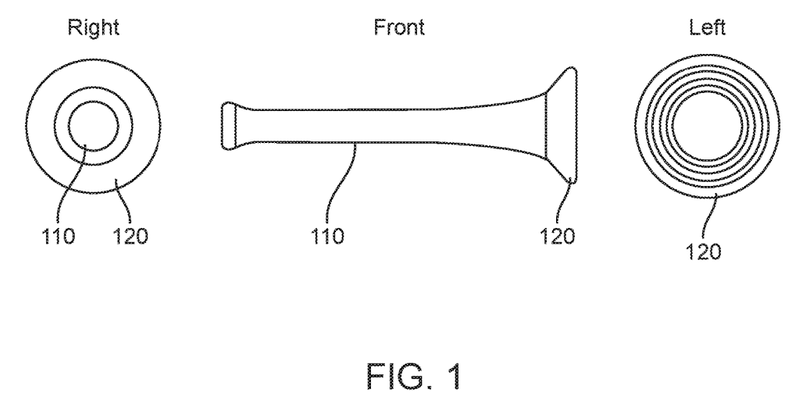
FIG. 1 illustrates an embodiment of the present invention in three views.
Figure 2:
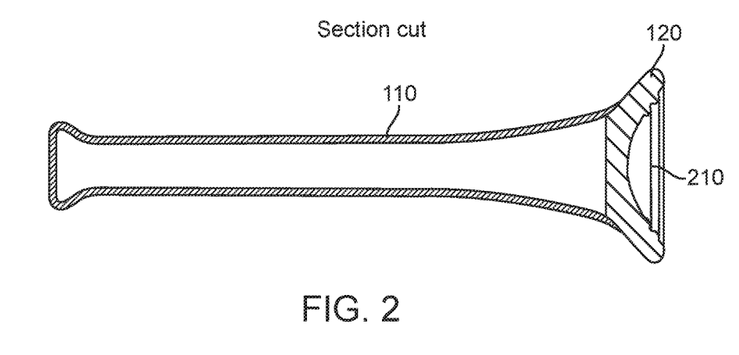
FIG. 2 illustrates the embodiment of FIG. 1 in section view.

FIG. 1 illustrates one embodiment of the invention in three views. As shown in FIG. 1, the device has a rigid shaft 110 terminating with a larger diameter concave end cup 120. The end cup is an elastically deformable material such that it can form to the shape of the walls of the vaginal canal. FIG. 2 show additional details of the device according to a first embodiment of the invention. As shown in FIG. 2, the end cup has a concave section 210 at the end to facilitate the collection of ejaculate.

Figure 3:
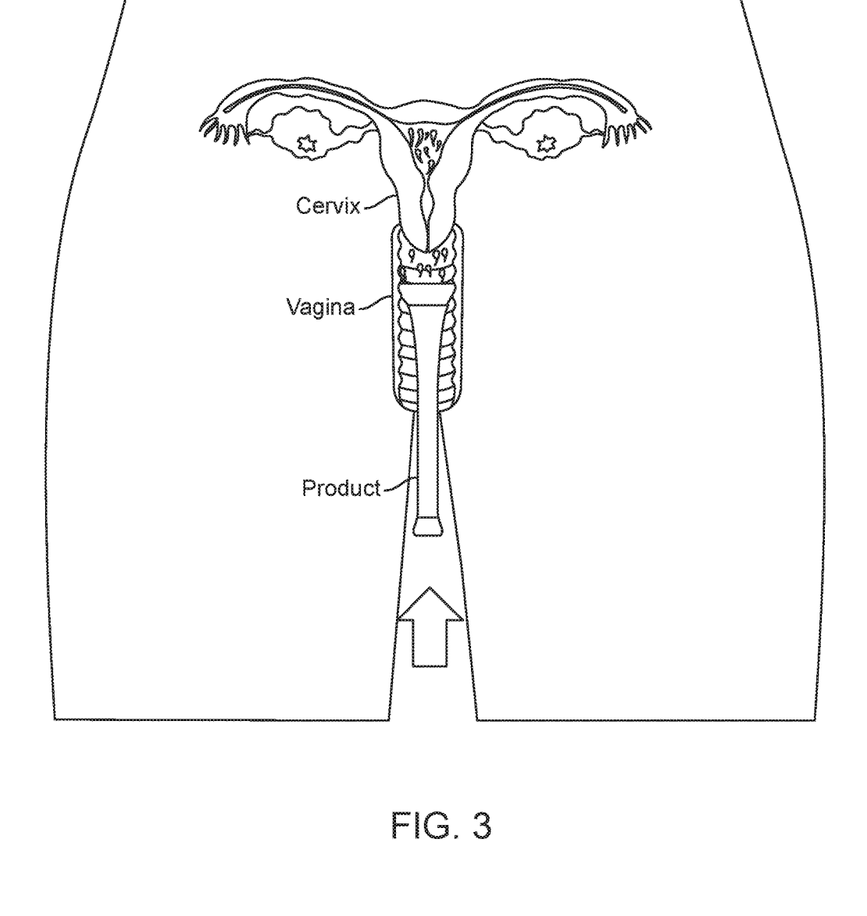
FIG. 3 is a diagram illustrating the use of the embodiment in FIG. 1.

FIG. 3 illustrates the use of the embodiment of the invention shown in FIGS. 1 and 2. After intercourse resulting in ejaculation, the cup end of the device is inserted into the vaginal opening and slid into a positions at the os of the cervix. As the device travels through the vaginal canal, the sides of the end cup 120 collect ejaculate present in the vaginal canal and present it to the cervix. The end cup 120 remains in the vicinity of the cervix for a prescribed amount of time, for example between ten minutes to several hours. After the time has passed, the device is removed by pulling the rigid shaft 110 until the end cup 120 clears the vaginal opening.

Figure 4:
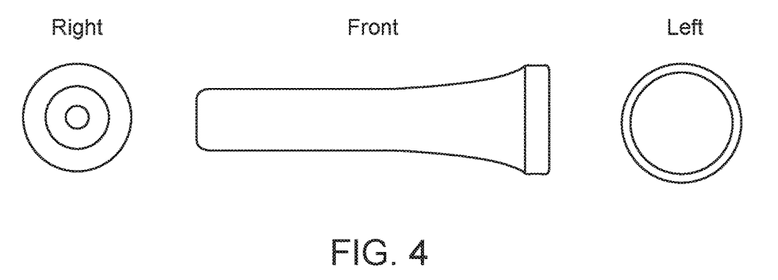
FIG. 4 illustrates another embodiment of the present invention in three views.
Figure 5:
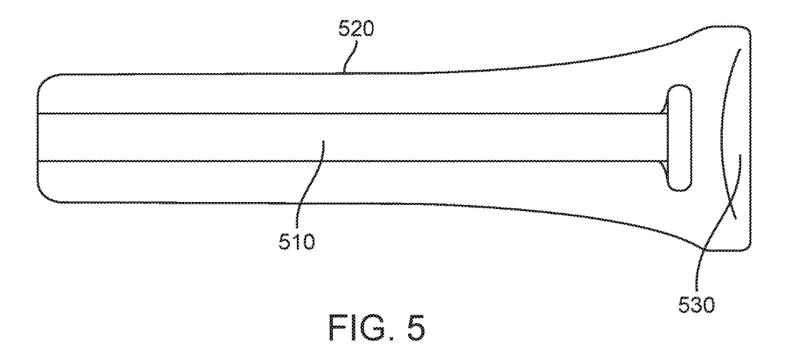
FIG. 5 illustrates the embodiment of FIG. 4 in section view.

FIGS. 4 and 5 illustrate a second embodiment of the invention, similar to the embodiment discussed in connection with FIG. 1. The key difference between the two embodiment is that the embodiment shown in FIGS. 4 and 5 is manufactured and assembled differently. As shown in FIG. 5, the device is comprised of a rigid shaft piece 510 and is covered with an elastically deformable material 520. The concave end cup 530 is formed using the deformable materials 520. Use of the device illustrated in FIGS. 4 and 5 is the same as described above for the embodiment shown in FIGS. 1 and 2.

Figure 6:
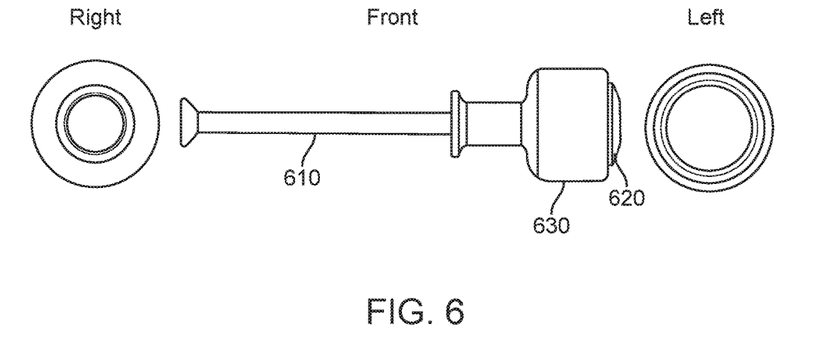
FIG. 6 illustrates another embodiment of the present invention in three views
Figure 7:
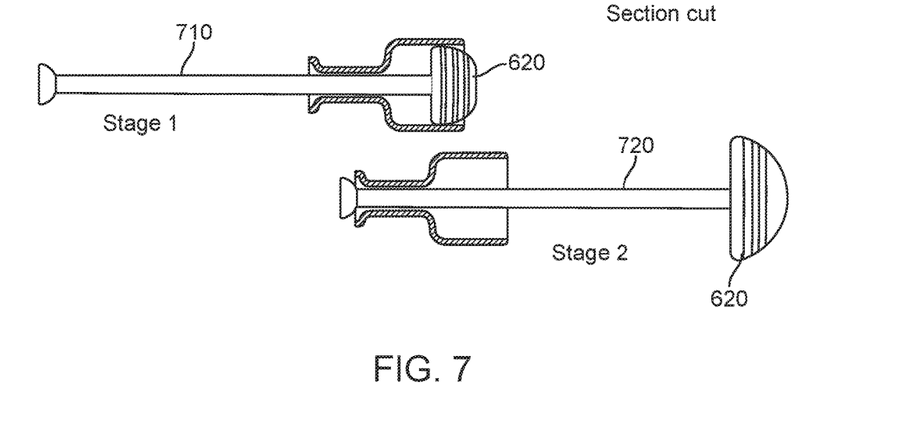
FIG. 7 illustrates the embodiment of FIG. 6 in section view.

FIGS. 6 and 7 illustrate a third embodiment of the present invention. FIG. 6 shows the device of the third embodiment prior to use. The device of FIG. 6 includes a shaft 610 and end cup 620, as well as a shell 630. The shaft 610 and shell 630 are made of rigid material; the end cup 620 is made of elastically deformable materials. The shaft protrudes through a hole in the shell 630 and connects to the end cup 620. When assembled prior to use, the wall of the end cup is compressed by the shell so as to present a small profile to the vaginal entrance. FIG. 7 illustrates the difference in profiles before and after actuation of the shaft 610. The top view 710 of FIG. 7 shows the device prior to insertion into the vaginal opening. The bottom view 720 shows the device after insertion into the vaginal opening and after actuation of the shaft. As can be seen in the top view 710, the overall device diameter is smaller than the diameter of the device when the shaft is actuated, owing to the expansion of the cup material after it clears the lip of the shell. In this way, the device diameter is smaller when it is inserted into the vaginal open, yet the end cup expands to effectively contact the vaginal walls to collect ejaculate.

Figure 8:
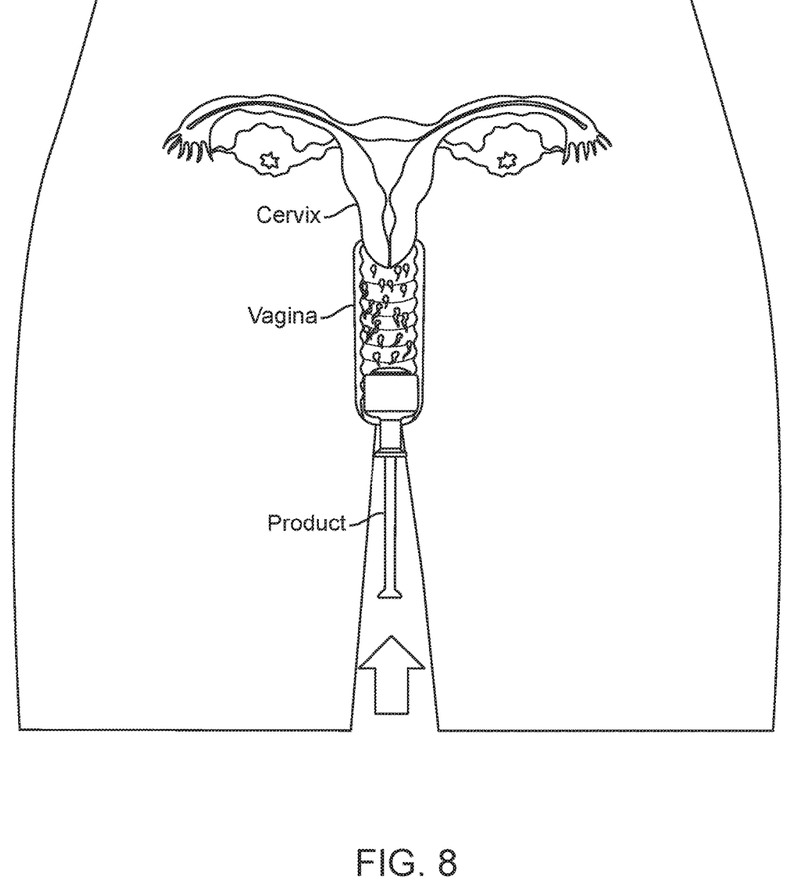
FIG. 8 is a diagram illustrating the use of the embodiment in FIG. 6.
Figure 9:
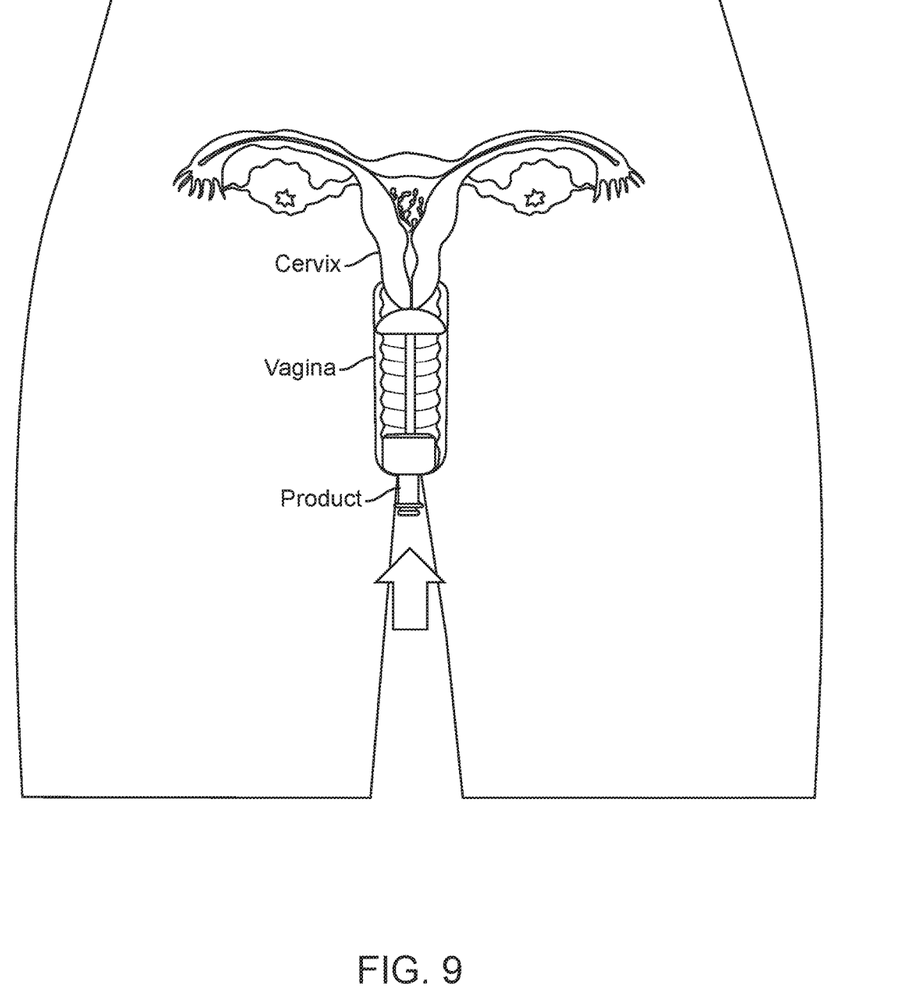
FIG. 9 is a diagram illustrating the use of the embodiment in FIG. 6.

FIGS. 8 and 9 illustrate the use of the device according to the embodiment shown in FIGS. 6 and 7. Similar to the first and second embodiments, the device of FIGS. 6 is inserted into the vaginal opening after intercourse and ejaculation. FIG. 8 shows the device after insertion into the vaginal opening. As shown in FIG. 8, the shell 630 of the device is placed in the vaginal opening and remains positioned there throughout use. Once the shell is seated into the vaginal opening, the shaft is actuated to deploy the end cup to its fullest diameter and move the end cup to the vicinity of the cervix. After deployment, the end cup 620 contacts the walls of the vaginal canal to collect ejaculate and present it to the os of the cervix, as shown in FIG. 9. The device remains in this position for the prescribed amount of time, between ten minutes and several hours.

Figure 10:
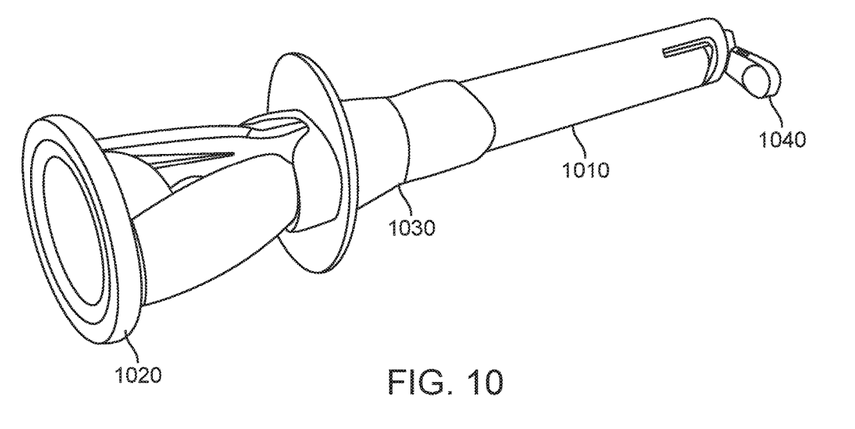
FIG. 10 illustrates another embodiment of the present invention.
Figure 11:
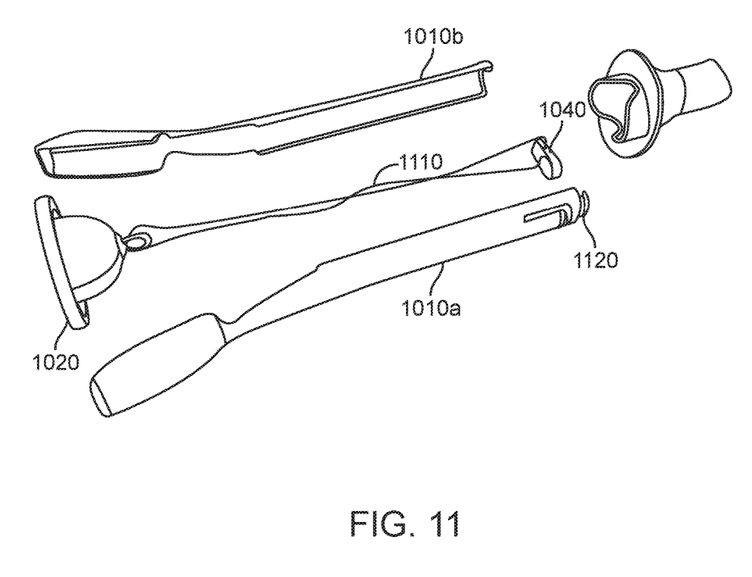
FIG. 11 illustrates various components of the embodiment of FIG. 10.

FIG. 10 illustrates a device according to a fourth embodiment of the present invention. The device of FIG. 10 has similar features to the other embodiments already discussed. The device has a shaft assembly 1010, a cup 1020, a shell 1030, and a wirelocker 1040. In this embodiment, the cup 1020 is designed to fold to present a smaller profile to the vaginal opening, and also to detach from the shaft 1010 and shell 1030 assembly. As shown in FIG. 11, the shaft assembly is comprised of two shaft halves, 1010a and 1010b. The cup 1020 is connected to the wirelocker 1040 by a wire-like linkage 1110 such as a length of wire or string. The wirelocker 1040 locks onto a locking feature 1120 on one side of the two-piece shaft 1010a, holding the cup 1020 in position at the end of the shaft assembly 1010 as shown in FIG. 10.

Figure 12:
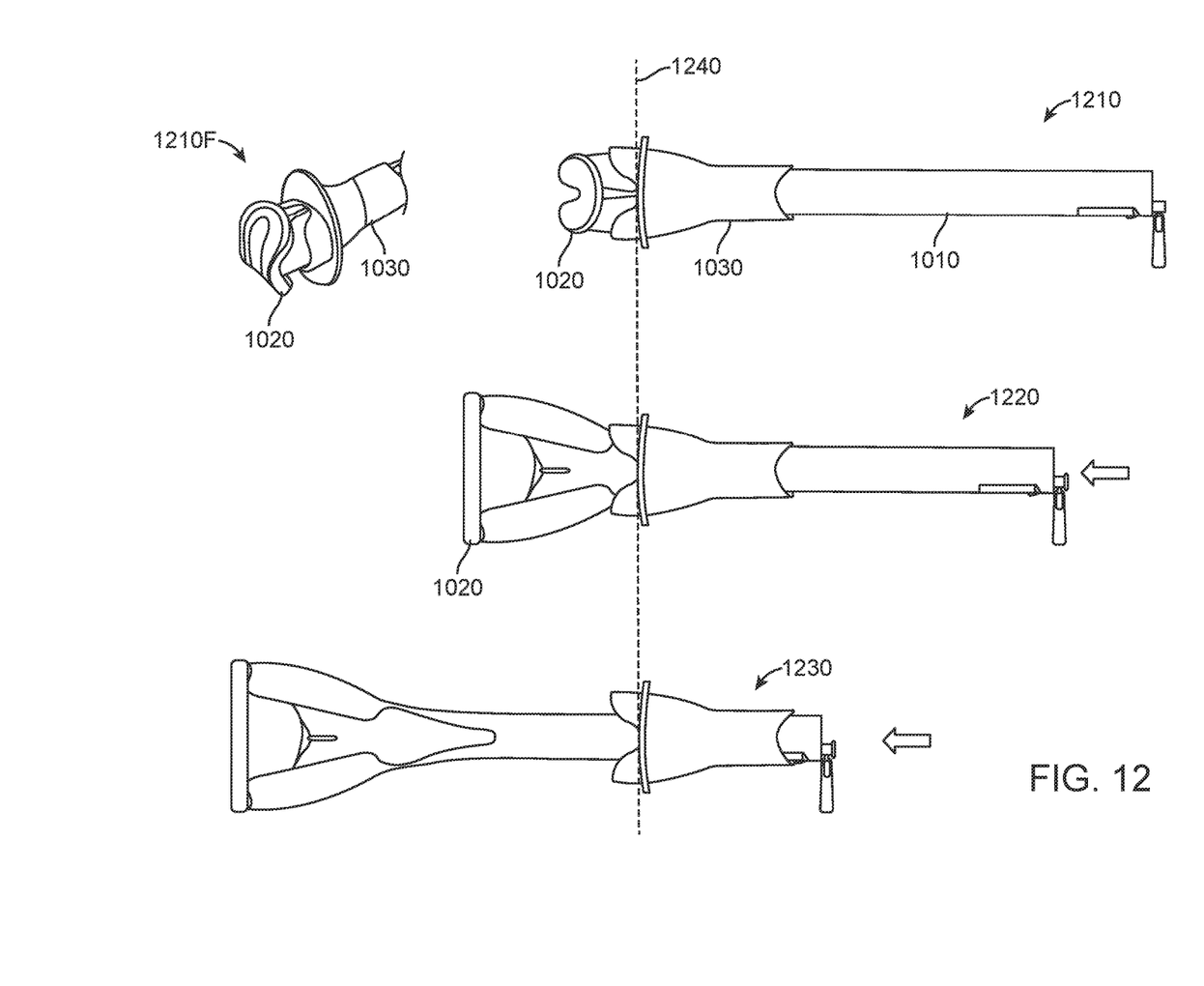
FIG. 12 is a diagram illustrating a use of the embodiment of FIG. 10.
Figure 13:
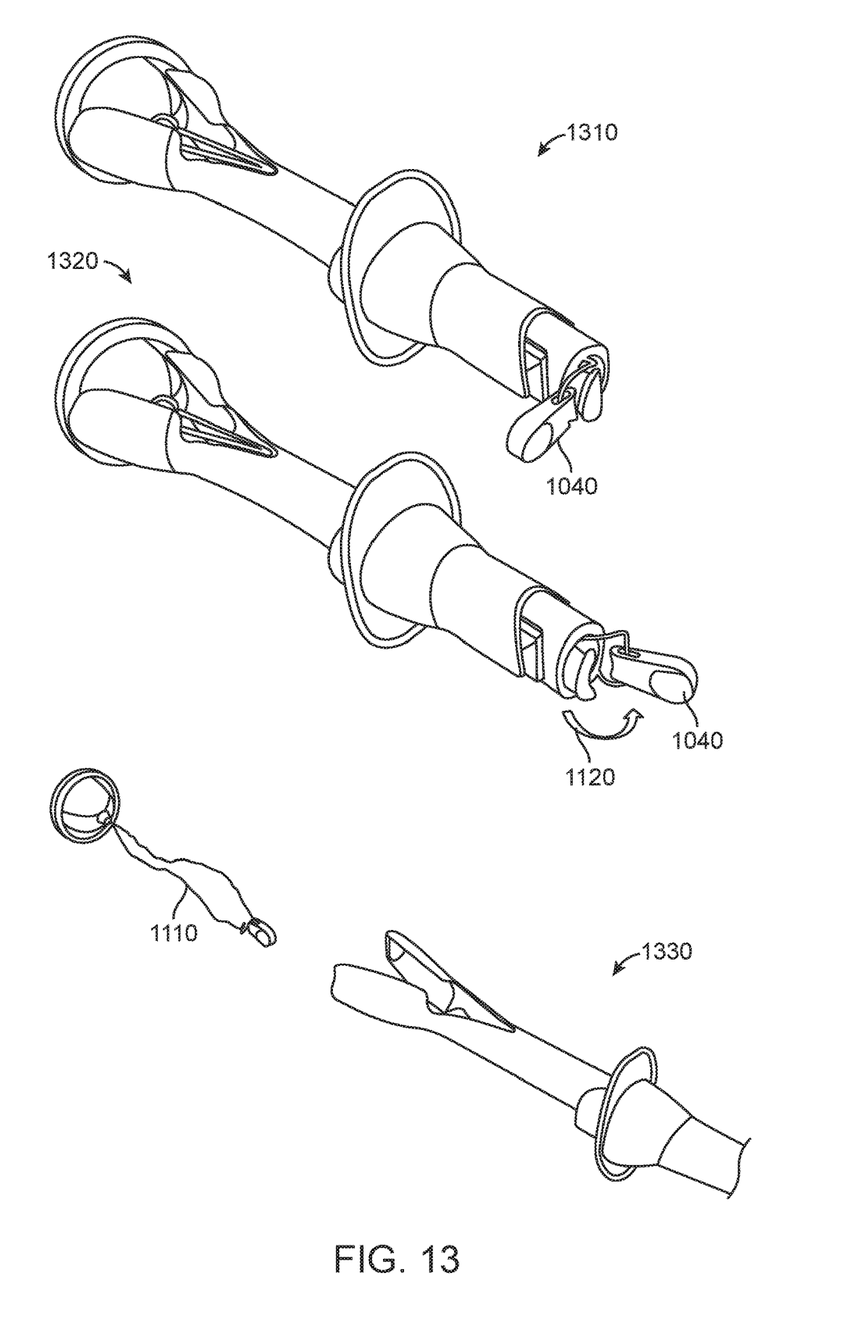
FIG. 13 is a diagram illustrating a different view of a use of the embodiment of FIG. 10.

FIGS. 12 and 13 illustrate the procedure for inserting the device according to the embodiment shown in FIG. 11 into the vaginal canal and placing the cup in proximity to the cervix. The top view 1210 of FIG. 12 shows the initial position of the device upon insertion into the vaginal opening, where dotted line 1240 indicates the exterior surface of the vaginal opening. As mentioned above, the end cup 1020 is folded by the shaft halves 1010a and 1010b to present a smaller profile to the vaginal opening. View 1210f shows the folded cup 1020 in the end of the shaft when the shaft is fully retracted into shell 1030 during insertion.

Once inserted and seated into the vaginal opening, the shaft is actuated in the direction of the vaginal canal as shown in the middle view 1220 of FIG. 12. As can be seen in the middle view 1220, as the shaft is longitudinally actuated through the shell, the two shaft halves allow the cup 1020 to expand to its full diameter and contact the walls of the vaginal canal. Continuing the procedure, the shaft is further actuated longitudinally until the cup reaches the os of the cervix as shown in bottom view 1230 of FIG. 12. As the cup travels through the vaginal canal, it contacts the walls of the vaginal canal collecting ejaculate and presenting it to the cervix.

FIG. 13 illustrated the procedure for detaching and deploying the end cup onto the cervix. In the top view 1310 of FIG. 13, the shaft of the device has been extended to reach the cervix. Wirelocker 1040 is shown at the external end of the shaft in the locked position, securing the end cup to the device. Middle view 1320 illustrated unlocking of the end cup by rotating the wirelocker 1040 to free it from the locking feature 1120. As shown in the bottom view of FIG. 13, once the wirelocker is removed from the locking feature 1120, it is free to pass through the shaft assembly 1010, detaching the end cup from the device. At this point, the shaft 1010 and shell 1030 assembly is removed from the vagina, leaving the end cup in the vicinity of the cervix. After the prescribed amount of time passes, the cup is removed using the wirelocker 1040 and wire-like linkage 1110.

What is claimed is:

1. An intravaginal device for improving fertility comprising:
   a rigid longitudinal shaft having a first and second end;
   a rigid shell with an opening through which the rigid longitudinal shaft passes and allows longitudinal movement of said shaft;
   a flexible end cup affixed to one end of the longitudinal shaft that compresses within the rigid shell so as to have a smaller outer diameter when compressed within the rigid shell than when deployed by longitudinal movement of the rigid shaft;
   wherein the flexible end cup outer diameter when deployed is sized to contact walls of a vaginal canal to collect ejaculate within the vaginal canal and present the ejaculate to a cervical os.

2. The intravaginal device of claim 1 wherein the flexible end cup is made of an elastically deformable material.

3. The intravaginal device of claim 1 wherein the shaft is plastic.

4. An intravaginal device for improving fertility comprising:
   a rigid shell having a longitudinal opening;
   a longitudinal shaft having a first and second end where the shaft is passed through the opening in the rigid shell so that the shaft is free to move longitudinally through the shell, the first end containing features that expand laterally and outward from a centerline of the shaft when the shaft is moved through the shell to a position where the features no longer interfere with the shell;

a flexible end cup positioned within the expandable features at the first end of the longitudinal shaft, the cup having a smaller outer diameter when the features are constrained within the shell and having a larger outer diameter when the features are moved to the position where the features no longer interfere with the shell;

a linkage attached to the flexible end cup at one end, and to a wirelocker on another end, running through the shaft, where the wirelocker engages a locking feature at the second end of the shaft thereby securing the flexible end cup within the features at the first end of the shaft by way of the linkage;

wherein the larger outer diameter of the flexible end cup is sized to contact walls of a vaginal canal to collect ejaculate within the vaginal canal and present the ejaculate to a cervical os.

5. The intravaginal device of claim 4, wherein the flexible end cup is released from the shaft when the wirelocker is freed from the locking feature.

6. The intravaginal device of claim 5, wherein the flexible end cup is configured to be removed from the vagina using the linkage.

7. The intravaginal device of claim 4, wherein one of the shaft or the shell is plastic.

8. The intravaginal device of claim 4, wherein the end cup is made from an elastically deformable material.

9. The intravaginal device of claim 4, wherein the linkage comprises a length of wire or string.

10. A method for improving fertility using an intravaginal device, wherein the method comprises the steps of:
- inserting a device having a longitudinal shaft connected to an end cup into a vaginal canal after intercourse;
- contacting the walls of the vaginal canal with the end cup made of a flexible material;
- longitudinally translating the shaft and end cup through the vaginal canal;
- collecting ejaculate with the end cup as the shaft and end cup is translated through the vaginal canal;
- presenting the ejaculate to a cervical os; and
- maintaining a greater amount of ejaculate in a vicinity of the cervical os than would be maintained without use of the intravaginal device.

11. The method of claim 10, further comprising expanding an outer diameter of the flexible end cup after the end cup exits a shell that constrains the end cup to a smaller outer diameter.

12. The method of claim 10, further comprising expanding the outer diameter of the flexible end cup when features on the shaft constraining the end cup to a smaller diameter exit a shell through which the shaft passes longitudinally.

13. The method of claim 10 wherein the end cup is maintained in a vicinity of the cervical os for a period of time not shorter than ten minutes, then is removed from the vagina.

* * * * *